United States Patent [19]

Drewlow

[11] Patent Number: Plant 6,004

[45] Date of Patent: Sep. 1, 1987

[54] IMPATIENS PLANT NAMED NOVA

[75] Inventor: Lyndon W. Drewlow, Ashtabula, Ohio

[73] Assignee: Mikkelsens, Inc., Ashtabula, Ohio

[21] Appl. No.: 786,127

[22] Filed: Oct. 10, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Schwartz, Jeffery, Schwaab, Mack, Blumenthal & Evans

[57] ABSTRACT

An Impatiens plant named Nova particularly characterized as to uniqueness by the combined characteristics of bright orange red flower color; relatively large flowers, two of which occur at each leaf axil; vigorous and superior self-branching habits; leaf variegation pattern and color, and relatively early flowering.

1 Drawing Figure

1

The present invention relates to a new and distinct cultivar of Impatiens plant, botanically known as Impatiens, names Nova. Nova was developed by me in Ashtabula, Ohio through controlled breeding by crossing Solared, disclosed in U.S. Plant Pat. No. 5,131 (seed parent) with Mikkelsen Seedling No. 83-803-2, an unnamed cultivar (pollen parent.)

Asexual reproduction by terminal or stem cuttings taken by me in Ashtabula, Ohio has shown that the unique features of this new Impatiens are stabilized and are reproduced true to type in successive propagations.

2

The following characteristics distinguish Nova from both its parent cultivars and other cultivated Impatiens of this type known and used in the floriculture industry:

1. Nova is deeper orange in color than Eclipse, disclosed in U.S. Plant Pat. No. 4,689, and similar in color to Solared. Under summer conditions Nova is brighter orange than Zenith (plant patent application pending), which fades to between 40C and 41B. Under winter conditions Nova and Zenith can be quite similar in color.

2. The flowers of Nova are larger than the flowers of

Solared and equal in size to the flowers of Eclipse, but with much better flower form. Flower size of Zenith is slightly larger than Nova.

3. The variegation color and pattern of Nova is similar to Enterprise (plant patent application pending), is deeper in color than Solared and Zenith, but not as dark as the non-variegated Eclipse leaves. Zenith has a distinct toothed pattern to variegation while the others have a smoother margin to variegation.

4. Nova is larger and more vigorous than Solared but not as large as Eclipse. Nova is similar in overall size to Zenith.

5. There are two flowers per leaf axil, which is similar to the female parent Solared. Eclipse and Zenith have only the flower per axil.

6. The leaf of Nova is longer and wider than Solared and Zenith, but not as large as the leaf of Eclipse. Leaf underside is reddish purple while Solared and Zenith are yellow green on the underside.

7. Flowering of Nova is 7 to 10 days earlier than either Eclipse or Enterprise, and similar to Zenith.

8. Nova is highly self-branched and vigorous, making it ideal for 4" pots, hanging baskets and bedding plant use.

9. Nova has shown tolerance to low temperature; plants performed well from a planting on May 15 when temperatures will still between 40° F. and 50° F.

10. Nova appears to require less water than most other cultivars; it was one of the last hanging baskets to wilt when seedlings were compared.

The accompanying colored photograph illustrates the overall appearance of this cultivar, showing the plant in perspective view with the colors being as true as it is reasonably possible to obtain in a colored reproduction of this type.

The following is a detailed description of my new impatiens cultivar based on plants produced under commercial practices in Ashtabula, Ohio. The photograph was taken in September of plants grown under greenhouse conditions. Color references are made to The Royal Horticultural Society Colour Chart except where general terms of ordinary dictionary significance are used.

Parentage: Controlled cross of Solared×Mikkelsen Seedling 83-802-2.

Propagation:

(A) *Type cutting.*—15 mm long will develop to 4–5 cm long in 18–21 days.

(B) *Time to root.*—8–10 days at 23° C. summer; 10–12 days at 20° C. winter.

(C) *Rooting habit.*—Heavy, fibrous.

Plant description:

(A) *Form.*—Symmetrically mounded, self-branching, compact, vigorous growing flowering herb; reddish purple stems.

(B) *Habit of growth.*—Continuous flowering, self-branching, compact, mounded, vigorous.

(C) *Foliage.*—Broad dark green leaves with greyed-purple veination; creamy yellow variegation approximately two thirds of the way up the leaves. (1) Size: 12 to 13 cm long and 3 to 3.5 cm wide on mature leaves. (2) Shape: Lanceolate with acuminate apex and acute base. (3) Texture: Upper hirsute and rugose, lower glabrous. (4) Margin: Serrated, finely ciliated. (5) Color: Young foliage top side, dark green with brownish red tinging; Young foliage under side, 183C; Mature foliage top side, 147A; Mature foliage under side, 183D. (6) Veination: pinnate, greyed-purple in color.

Flowering description:

(A) *Flowering habits.*—Flowers continuously from leaf whorl in progressively orderly manner with usually two flowers per axil. All first flowers from axil open before second flowers start to open, at which time first flowers or the whorl above start opening. Takes 5 to 7 days from bud to bloom; flowers last 2 to 3 weeks.

(B) *Natural flowering season.*—Indeterminant and continuous. Quantity of flowering increases with increasing levels of light.

(C) *Flower buds.*—Ellipsoidal, flowers perfect; reddish spur up to 4 cm long on mature bud with throat behind ovary and originating from major sepal.

(D) *Flowers born.*—On individual short pedicels from whorl of usually five leaves, flowering progressively around the whorl, with the second flower from an axil not opening until all first flowers have opened. First flowers are carried above foliage while second flowers from axil in whorl are in the canopy.

(E) *Quantity of flowers.*—Very floriferous due to multiple flowering from axil.

(F) *Petals.*—(1) Shape: Heart shaped, with upper petal slightly larger. (2) Color top side when opening: bright luminescence orange red close to 33A, fading to 33A-B; under side 33A, fading to 33B. (3) Number of petals: Five. (4) Size of flowers: 5 to 5.5 cm.

(G) *Reproductive organs.*—(1) Stamens: Five in number. (a) Anther shape: Hooded, greenish white. (b) Pollen color: Cream. (2) Pistels: Five. (a) Stigma shape: Segmented, column shaped; purple tinge. (b) Style color: Purple tinge. (c) Ovaries: Five in number, celled, size 5 mm until fertilized.

Disease resistance: No significant disease problems noted to date. Nova appears to be more resistant to spider mites due to the hairs on upper leaf surface.

I claim:

1. A new and distinct cultivar of Impatiens named Nova, as described and illustrated, and particularly characterized by the combined features of bright orange red flower color; relatively large flowers, two of which occur at each leaf axil; vigorous and superior self branching habits; leaf variegation pattern and color, and relatively early flowering.

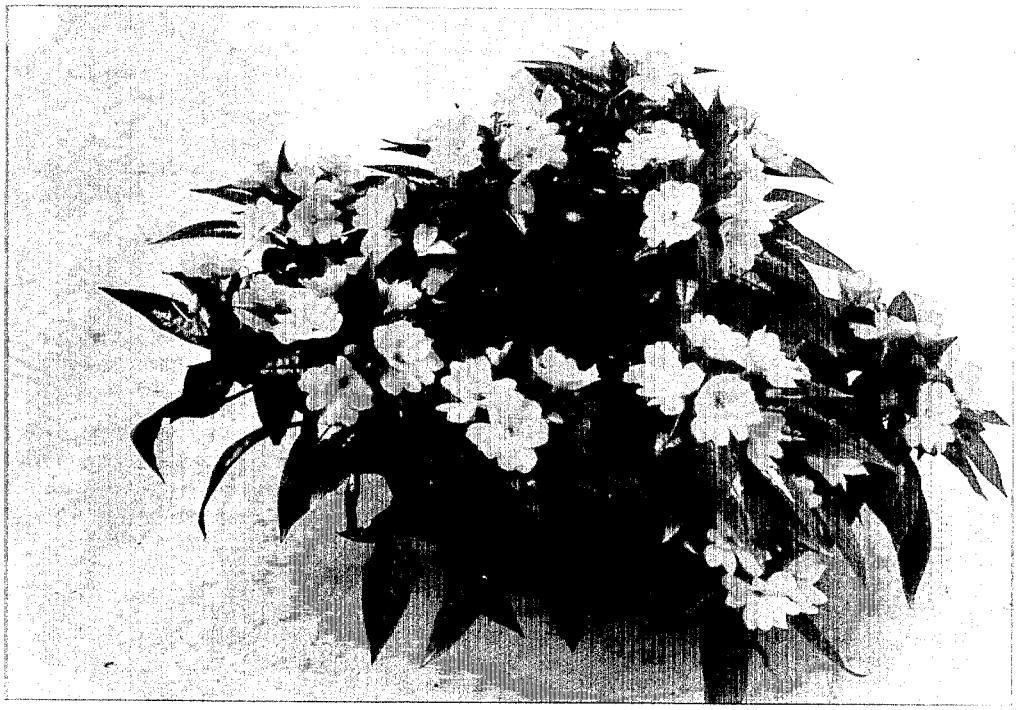

* * * * *